United States Patent [19]

Tamai et al.

[11] Patent Number: 5,298,402
[45] Date of Patent: Mar. 29, 1994

[54] CELL LINES PRODUCED BY TRANSFORMING LEUKOCYTES OF FISH WITH ONCOGENES AND PHYSIOLOGICALLY ACTIVE SUBSTANCES PRODUCED BY THE CELL LINES

[75] Inventors: Tadakazu Tamai, Tsukuba; Hiroki Murakami, Fukuoka; Nobuyuki Sato, Tsukuba; Shoji Kimura, Tsukuba; Yasuhiko Sasamoto, Tsukuba, all of Japan

[73] Assignee: Taiyo Fishery Co., Ltd., Tokyo, Japan

[21] Appl. No.: 844,851

[22] Filed: Mar. 3, 1992

[30] Foreign Application Priority Data

Mar. 4, 1991 [JP] Japan .................................. 3-37541

[51] Int. Cl.$^5$ .................. C12N 15/06; C12N 5/16
[52] U.S. Cl. ........................ 435/172.3; 435/240.2; 935/66; 935/70
[58] Field of Search ............... 435/69.1, 69.2, 69.4, 435/69.5, 69.51, 69.52, 240.21; 935/59, 70

[56] References Cited

U.S. PATENT DOCUMENTS 4,652,522  3/1987  Kennett et al. .

OTHER PUBLICATIONS

Siegel et al. 1973 in Tissue Culture: methods & applications (ed) Kruse et al. New York: Academic Press pp. 135–138.

American Type Culture Collection Catalogue of Cell Lines and Hybridomas, 7th ed. 1992 see species index pp. 464–477.

Michael G. Reth, Patrizia Ammirati, Sharon Jackson & Frederick W. Alt, "Regulated progression of a cultured pre-B-cell line to the B-cell stage," Nature, vol. 317, Sep. 26, 1985, pp. 353–355.

*Primary Examiner*—Charles L. Patterson, Jr.
*Assistant Examiner*—G. E. Bugaisky
*Attorney, Agent, or Firm*—Limbach & Limbach

[57] ABSTRACT

The present invention provides cell lines capable of indefinite growth which are produced by transforming leukocytes isolated from peripheral blood of fish with a oncogene, a method of establishing the cell line, a method of recovering immunologically active substances from the culture of the cell lines. It has been difficult to maintain continuous cultures of fish leukocytes. The present invention provides cell lines capable of indefinite growth and a method of producing immunologically active substances, e.g., immunologically acitive substances, using these cell lines.

4 Claims, 2 Drawing Sheets

CELL LINES PRODUCED BY TRANSFORMING LEUKOCYTES OF FISH WITH ONCOGENES AND PHYSIOLOGICALLY ACTIVE SUBSTANCES PRODUCED BY THE CELL LINES

FIELD OF THE INVENTION

The present invention relates to novel cell lines capable of indefinite growth, a method of establishing the cell lines and to a method of producing immunologically active substances by culturing the cell lines.

BACKGROUND OF THE INVENTION

Fish disease and injuries pose serious problems in the cultivation of various species of fish. Fish disease can spread to aquaculture, which is the husbandry of aquatic animals and plants, and cause to kill all the fish in aquaculture, which results in devastating damage to aquaculture. Contamination of infectious agents in aquaculture make it impossible to culture fish in the same facilities again. These problems have been a major problem of stable supply of fish. In addition, to prevent and treat fish disease, a large amount of antibiotics has been used for culturing fish, and the use of a large amount of antibiotics may cause problems in human health. To prevent or solve these problems, the present inventors have contemplated a method for enhancing a self defense system of fish by externally administering immunologically active substances to fish. These substances are originally secreted out from the leukocytes of fish so that it is necessary to isolate such cells from fish to establish a cell line. The cell line should be capable of indefinite growth and of producing immunologically active substances.

There have been various methods of obtaining cell lines capable of indefinite growth. These methods use hybridomas that tumor cells fused with lympocytes obtained from human (Kohler, G. et al., 1975, Nature 256: 495), transformants that are produced by transforming cells with tumor causing herpesvirus or EBV (Epstein, M. A., & Achong, B. G., 1979, *The Epstein-Barr Virus* Springer-Verglag, Berlin), T lymphocytes transformed with HTLV-1 (Sugamura, K., et al., 1984, J. Immunol. Methods, 34: 221) and pre-B cells transformed with Ab-MLV (Reth, M. G., et al., 1985, 317:353). Cells derived from B lymphocytes are useful for producing hybridomas while T lymphocytes and leukocytes are not suitable for producing hybridomas. In fact, there has been no report on hybridomas produced from these cells so far. Serious drawbacks of hybridomas produced by cell fusion are their instability and undesirable changes in their properties during culture and subculture. Transformation is useful for producing transformants from leukocytes using various viruses. The transformants, however, also have properties of viruses so that the properties of the transformants are totally different from those of the original cells.

SUMMARY OF THE INVENTION

Leukocytes of fish have been difficult for continuous culture. The present invention provides cell lines capable of indefinite growth which are produced by transforming the leukocytes of fish with oncogenes and a method of producing immunologically acitive substances using these cell lines.

DETAILED DESCRIPTION OF THE INVENTION

Figure 1:
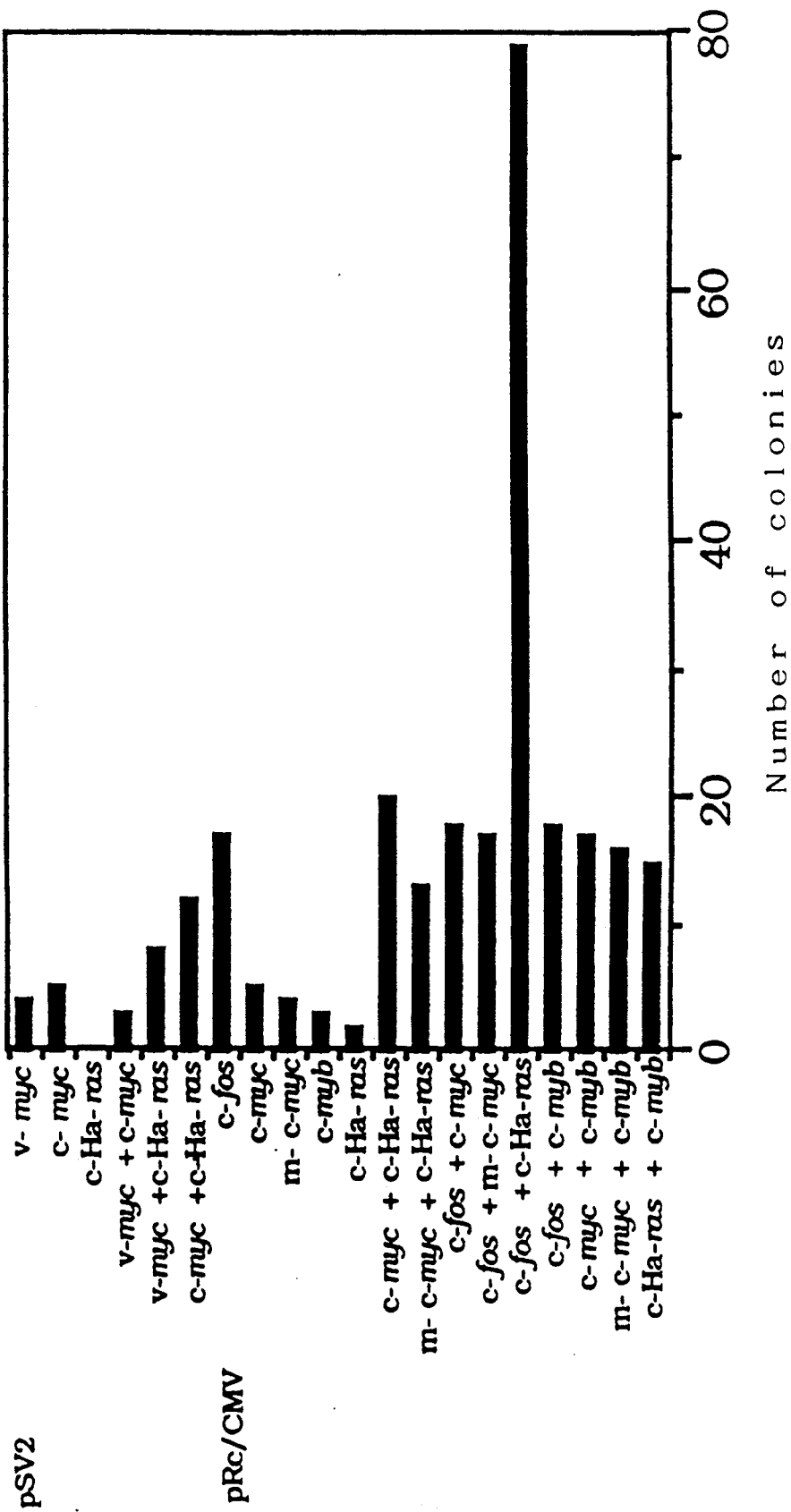
FIG. 1 is a graph showing the number of foci and cell lines capable of indefinite growth.

An object of the present invention is to provide cell lines capable of growing indefinitely and of secreting immunologically active substances under a given condition and a method of establishing the cell lines.

The present inventors have isolated leukocytes from fish, transformed the leukocytes with oncogenes, produced a novel cell line capable of indefinite growth without losing the original properties of the leukocytes and successfully produced immunologically active substances from the novel cell lines.

The present invention provides;

(1) a cell line capable of indefinite growth which is produced by transforming a leukocyte, isolated from peripheral blood of fish, with an oncogene, (2) a method of establishing a cell line capable of indefinite growth comprising isolating a leukocyte from peripheral blood of fish, transforming the leukocyte with an expression plasmid containing an oncogene and continuously culturing the cell containing the plasmid, (3) the cell line capable of indefinite growth according to (1) in which the oncogene comprises two or more different kinds of oncogenes, and (4) a method of producing immunologically active substances comprising culturing the cell line according to (1) and (3) and recovering immunologically active substances produced by the cell line from the culture.

A method of producing cell lines capable of indefinite growth is as follows. The cell lines are derived from leukocytes isolated from the peripheral blood of fish. Oncogenes are introduced into the leukocytes to give transformants. Cell lines capable of indefinite growth are selected from the transformants and continuously cultured to give cell lines capable of indefinite growth.

Leukocytes of the present invention are defined as cells that are found in blood of fish and lacks a respiratory pigment, and include polymorphonuclear leukocytes, lymphocytes and monocytes. Any fish can be candidates to obtain blood, including a halibut, a sea bream, a blowfish and a shark. Among varieties of fishes, fish suitable for culture, such as a halibut and a sea bream, is also suitable to obtain blood. Blood is removed from fish by methods known in the art. For example, peripheral blood is removed by a heparin treated syringe from the vein of fish under anesthesia. Red blood cells are removed from the blood by centrifugation at 1,500 rpm for 40 minutes and a lymphocyte fraction was saved. Lymphocytes in the lymphocyte fraction are then continuously cultured under an appropriate condition to give cells to be used in the subsequent step. Alternatively, lymphocytes in the lymphocyte fraction can be directly used in the subsequent step.

Oncogenes are introduced into the leukocytes by expression plasmids containing oncogenes. Any expression plasmids can be used as far as plasmids are capable of introducing themselves into the cells and expressing oncogenes in the cells. In expression plasmids, oncogenes are inserted into the downstream of a promoter, which allows to express the genes. In addition, expression plasmids may further comprise RNA splicing sites and polyadenylation sites. Promoters that express oncogenes in expression plasmids include SV40E promoter (M. Fried, et al.,: Cancer Cells 4 ed., M. Batchan, et al., 1986, p 1-16, Cold Spring Harbor Laboratory, New York) and CMV promoter (supra). Expression plasmids containing promoters include pSV2 neo (Jimenez, A., et al., 1980, Nature, p 281-869) and pRcCMV (Kelvin M. Kluccher et al., 1989, J. Virology, p 5334-5343). Oncogenes are incorporated into these vectors by methods known in the art. The vectors are then introduced into leukocytes. Oncogenes inserted into plasmids are derived from any animal species and can be any type including viral oncogenes and cellular oncogenes. These oncogenes include v-myc (M. Bishop Vennslorm et al., 1981, J. Virol. 39: 631 and DNAS 80, 1983, p 100-104), v-myb (K. H. Klempnauer, et al and Cell, 1982, 31: 453-463), c-fos (F. Van Strauten., et al., 1983 Proc.Natl.Acad.Sci. U.S.A. 80: 3183-3187), cHa-ras (O. J. Cupon., et al., 1983, Nature 302: 33-37), h-c-myc (W. W. Colby., et al., 1983, Nature 301: 722-725), m-c-myc (O. Bernard, et al., 1983, EMBO J. 2: 2375-2383) and c-myb (K. H. Klempnauer, et al., 1982, Cell 31: 453-463).

Oncogenes can be obtained from animal cells, a source of oncogenes, and viral DNA by methods known in the art. Oncogenes can be prepared by amplifying oncogenes by a PCR method (Saiki, R. K., et al., 1985, Science 37: 170) or by growing a clone containing a desired oncogene in a gene library that is constructed by a shot-gun method (L. Clarke, 1976, Cell 9: 91) or by chemically synthesizing a whole sequence by a phosphate triester method (1984, Nature 310: 105).

To clone oncogenes, methods known in the art may be utilized: restriction enzymes for digestion of DNA, DNA ligase for ligation, polynucleotide kinase, DNA polymerase and a chemically synthesized linker. These materials are commercially available or easily made in the laboratory. Some oncogenes are already incorporated into expression vectors, which are used to introduce oncogenes into cells and can be also used in the present invention. These expression plasmids include pSVc-myc (Nature, 1983, 304: 596-602), pSVvmyc (Lond et al., 1983, Nature 304: 596).

Oncogenes are introduced into leukocytes by methods known in the art. Such methods include, but are not limited to, an electroporation method (Neumann E., et al., Gene transfer into mouse myeloma cells by electroporation in a high electric field, EMBO J. 1: 841), a calcium phosphate method (Graham, F. L., et al., 1973, Virology, 52: 456), a DEAE dextran method (Mccutchan, J. H., et al., 1968, J. Natl. Cancer Inst., 41: 351), a microinjection method (K. Ozato, et al., 1986, Cell differ. 19: 237), a ghost red cell method (Malone, R. W., et al., 1989, Proc. Natl. Acad. Sci. U.S.A., 86: 6077). In an electroporation method, transformation efficiency is dependent upon a pulse width, a pulse magnitude, a cell density and concentration of DNA to be used for introduction. Suitable conditions are as follows: a pulse width; 10–100μ second, a pulse magnitude; 3–70 KV, cell density; $10^4$ or more cell/ml, concentration of DNA; 0.1–500 μg/$10^7$ cell.

Types of oncogenes and the number of oncogenes to be introduced are not limited to specific oncogenes and the specific number of oncogenes. However, if a single oncogene, three or more oncogenes, or two identical oncogenes are introduced into cells, the long-term immortality of cells are jeopardized. Preferably, cellular oncogenes derived from human beings and a combination of two different kinds of oncogenes produce good results. Specifically, a combination of human c-fos and human c-Ha-ras or a combination of h-c-myc and human c-Ha-ras is suitable for introduction. More than one oncogenes are introduced into a single vector. A combination of vectors, each containing a single oncogene are preferably used. Vectors containing oncogenes, each containing more than one oncogenes, can be potential vectors for introduction. Such vectors, however, are not easily constructed and may have problems in gene expression in host cells.

Leukocyte transformants containing oncogenes thus obtained are continuously cultured by methods known in the art to establish cell lines capable of indefinite growth. The cell lines thus established are used to produce physiologically active substances by culturing them in a culture medium. Culture media, which are those typically used for culturing animal cells, include ERDF medium (Nippon Suisan Kagaku, 1987, 55(4): 525-527, MEM medium, RPMI-1640 medium, L-15 medium, E-12 medium and the like.

Physiologically active substances produced by the established cell lines are accumulated inside or outside of the cells and are purified by the typical purification methods of proteins. The proteins are precipitated by salting-out or using organic solvents. Isolation and purification are carried out by liquid chromatography, ion-exchange chromatography, adsorption chromatography, affinity chromatography, gel filtration, dialysis, electrophoresis and a combination thereof.

EXAMPLE

The present invention will be further illustrated by the following Examples. The Examples are not intended to limit the scope of the present invention.

EXAMPLE 1

[1] Construction of Vectors for Introducing Oncogenes into Host Cells

[1]-(1) Construction of human c-fos inserted pRC/CMV

1 μg of human human c-fos [Co No. 026.,(Cancer oncogene)] was digested with 10 units of EcoRI (TAKARA SHUZO Co., LTD) at 37° C. for three hours. After digestion, the reaction product was electrophoresed on an agarose gel. A 2619 bp DNA fragment obtained from the gel and 1 μg of Bluescript EcoRI fragment (Stratagene) were combined. 10 units of T4 DNA ligase (TAKARA SHUZO Co., LTD) was added to the mixture and the mixture was incubated at 15° C. for three hours. 1 μg of the construct thus obtained was digested with 1 unit of NotI (TAKARA SHUZO Co., LTD) and 1 unit of XbaI (TAKARA SHUZO Co., LTD) at 37° C. for three hours. After digestion, a 5 kbp restriction fragment was obtained. The 5 kbp restriction fragment and 1 μg of the NotI/XbaI fragment of pRc/CMV (In vitrogene) were combined. 10 units of T4 DNA ligase was added to the mixture. The mixture was incubated at 15° C. for three hours. After ligation, 1 μg of pRC/CMX containing human c-fos was obtained.

[1]-(2) Construction of human c-Ha-ras inserted pRC/CMV

1 μg of human c-Ha-ras (ATCC No. 19002) was digested with 10 units of EcoRI(TAKARA SHUZO Co., LTD) at 37° C. for three hours. After digestion, the reaction product was electrophoresed on an agarose gel. A 460 bp DNA fragment obtained from the gel and 1 μg of Bluescript EcoRI fragment (Stratagene) were combined. 10 units of T4 DNA ligase (TAKARA SHUZO Co., LTD) was added to the mixture and the ligation mixture was incubated at 15° C. for three hours. 1 μg of the construct thus obtained was digested with 1 unit of BamHI (TAKARA SHUZO Co., LTD) at 37° C. for three hours. After digestion, a 0.5 kbp restriction fragment was obtained. The 0.5 kbp restriction fragment and the BamHI/BamHI fragment of pRC/CMV (In vitrogene) were combined. 10 units of T4 DNA ligase was added to the mixture. The ligation mixture was incubated at 15° C. for three hours. After ligation, 1 μg of pRC/CMX containing human c-Ha-ras was obtained.

[1]-(3) Construction of human c-myc inserted pRC/CMV

1 μg of human c-myc (ATCC No. 12301) was digested with 10 units of HindIII (TAKARA SHUZO Co., LTD) and 10 units of EcoRI (TAKARA SHUZO Co., LTD) at 37° C. for three hours. After digestion, the reaction product was electrophoresed on an agarose gel. A 850 bp DNA fragment obtained from the gel and 1 μg of Bluescript HindIII/EcoRI fragment (Stratagene) were combined. 10 units of T4 DNA ligase (TAKARA SHUZO Co., LTD) was added to the mixture and the ligation mixture was incubated at 15° C. for three hours. 1 μg of the construct thus obtained was digested with 1 unit of XbaI (TAKARA SHUZO Co., LTD) and 1 unit of EcoRI (TAKARA SHUZO Co., LTD) at 37° C. for three hours. After digestion, a 9 kbp restriction fragment was obtained. The 9 kbp restriction fragment and the EcoRI/XbaI fragment of pRC/CMV were combined. 10 units of T4 DNA ligase was added to the mixture. The ligation mixture was incubated at 15° C. for three hours. After ligation, 1 μg of pRC/CMX containing human c-myc was obtained.

Mouse (m-1) c-myc inserted pRC/CMV and human c-myb (Co No. 071) inserted pRC/CMV were also constructed by the method described in [1]-(1), -(2), -(3).

[1]-(4) Construction of human c-myc inserted pSV2

1 μg of human c-myc (ATCC No. 12301) was digested as described in [1]-(3). The restriction fragment was ligated to Bluescript fragment. 1 μg of the construct was digested with 10 units of HindIII and 10 units of BglII at 37° C. for three hours. A 9 kbp fragment thus obtained was combined with 1 μg of a HindIII/BglII digested pSV2 fragment. 10 units of T4 DNA ligase (TAKARA SHUZO Co., LTD) was added to the mixture and the ligation mixture was incubated at 15° C. for three hours. 1 μg of pSV2 containing human c-myc was obtained.

[1]-(5) Construction of human c-Ha-ras inserted pSV2

1 μg of human c-Ha-ras (ATCC) was digested as described in [1]-(2). After digestion, the restriction fragment was ligated to Bluescript fragment. 1 μg of the construct thus obtained was digested with 10 unit of EcoRI (TAKARA SHUZO Co., LTD) at 37° C. for three hours. After digestion, a 0.5 kbp restriction fragment was obtained. The 0.5 kbp restriction fragment and the EcoRI digested pSV2 were combined. 10 units of T4 DNA ligase was added to the mixture. The ligation mixture was incubated at 15° C. for three hours. 1 μg of pSV2 containing human c-Ha-ras was obtained.

V-myc (ATCC No 20852) inserted pSV2 was also constructed by the method described in [1]-(1), -(2).

[2] Establishment of Cell Lines Containing Oncogenes 10 ml of blood was obtained from the vein of a halibut (about 750 g in weight) using a 10 ml heparin treated syringe. 20 ml of the blood diluted 4-fold with an ERDF medium containing sodium salts of heparic acid was gently overlayed onto the surface of 15 ml of Lymphocyte Separation medium (Pharmacia) in a plastic centrifuge tube. The tube was centrifuged at 1,500 rpm for 15 minutes at room temperature. After centrifugation, the lympocyte fraction was transferred to a fresh centrifuge tube, washed with an ERDF medium and centrifuged at 1,500 rpm for 15 minutes at room temperature. The red blood cells were almost all removed by the procedure described above. The lymphocytes thus obtained was suspended in an ERDF medium. The suspension was added to 10 ml of an ERDF medium containing 10% fetal calf serum. The mixture was then placed in a 10 ml plastic petri dish to a final density of $3.5 \times 10^6$ cell/ml. The lymphocytes were incubated at 15° C., 5% $CO_2$ in a $CO_2$ incubator. A half of the culture medium was changed every three days. Desired lymphocytes were obtained after the culture.

An appropriate promoter was inserted into the upstream of the 5' end of the oncogene in a plasmid vector constructed in [1]. The plasmid vector was introduced into the lymphocytes (first passage) by electroporation. More specifically, introduction was carried out as follows.

The lymphocytes were suspended in 3.5 ml of 0.2 mM Tris-HCl buffer/pH 7.4 containing 0.25M mannitol, 0.1 mM calcium chloride, 0.1 mM magnesium chloride. The plasmid vector was added to the suspension and the mixture was left standing in a cell chamber for 5 minutes.

Electroporation was carried out under the following condition: a pulse width; 30μ second, a pulse magnitude; 13 KV, cell density; $4 \times 10^4$ cell/ml, concentration of DNA; 250 μg/$10^7$ cell. Mutant lymphocytes transformed by the oncogene vigorously grew and formed a focus, aggregation of cells. The foci were counted and a frequency of the cells capable of indefinite growth was calculated. The results are shown in FIG. 1.

When vector pSV2 is used, transformation of the cells with a combination of human c-myc inserted pSV2 and human c-Ha-ras inserted pSV2 produces many desired cells. In contrast, when vector pRC/CMV is used, a combination of human c-myc inserted pRC/CMV and human c-Ha-ras inserted pRC/CMV produces desired cells with the highest frequency and a combination of human c-fos inserted pRC/CMV and human c-Ha-ras inserted pRC/CMV produces desired cells with the secondly highest frequency.

The cells transformed with oncogenes were continuously cultured in an EDRF medium containing 10% fetal calf serum at 15° C., 5% $CO_2$ in a $CO_2$ incubator and the number of days was counted for viable cells. Table 1 shows the results.

TABLE 1

| Effects of oncogenes on viability of leukocytes | | |
|---|---|---|
| | Number of colonies | |
| Plasmid | 10 days | 3 month |
| pSV2 | | |
| v-myc | 4 | — |
| c-myc | 5 | — |
| c-Ha-ras | — | — |
| v-myc + c-Ha-ras | 8 | — |

TABLE 1-continued

Effects of oncogenes on viability of leukocytes

| Plasmid | Number of colonies | |
|---|---|---|
| | 10 days | 3 month |
| c-myc + c-Ha-ras pCMV | 12 | — |
| c-fos | 16 | — |
| h-c-myc | 4 | — |
| m-c-myc | 3 | — |
| c-myb | 2 | — |
| c-Ha-ras | 1 | — |
| h-c-myc + c-Ha-ras | 20 | 11 |
| m-c-myc + c-Ha-ras | 10 | — |
| c-fos + h-c-myc | 16 | — |
| c-fos + m-c-myc | 13 | — |
| c-fos + c-Ha-ras | 79 | 25 |
| c-fos + c-myb | 17 | — |
| h-c-myc + c-myb | 15 | — |
| m-c-myc + c-myb | 13 | — |
| c-Ha-ras + c-myb | 7 | — |

As is evident from the Table 1, cells containing a combination of human c-fos inserted pRC/CMV and human c-Ha-ras inserted pRC/CMV and cells containing a combination of human c-myc inserted pRC/CMV and human c-Ha-ras inserted pRC/CMV have the ability to survive even after three months of culture: almost all these cells are viable and capable of indefinite growth. Other transformants also survived for a long period of time. One of the transformants containing human c-fos inserted pRC/CMV and human c-Ha-ras inserted pRC/CMV was designated POL-001, a novel cell line.

Cell line POL-001 containing human c-fos inserted pRC/CMV and human c-Ha-ras inserted pRC/CMV was deposited with Fermentation Research Institute, Agency of Industrial Science and Technology and was assigned the accession number FERM BP-3742.

EXAMPLE 2

Figure 2:
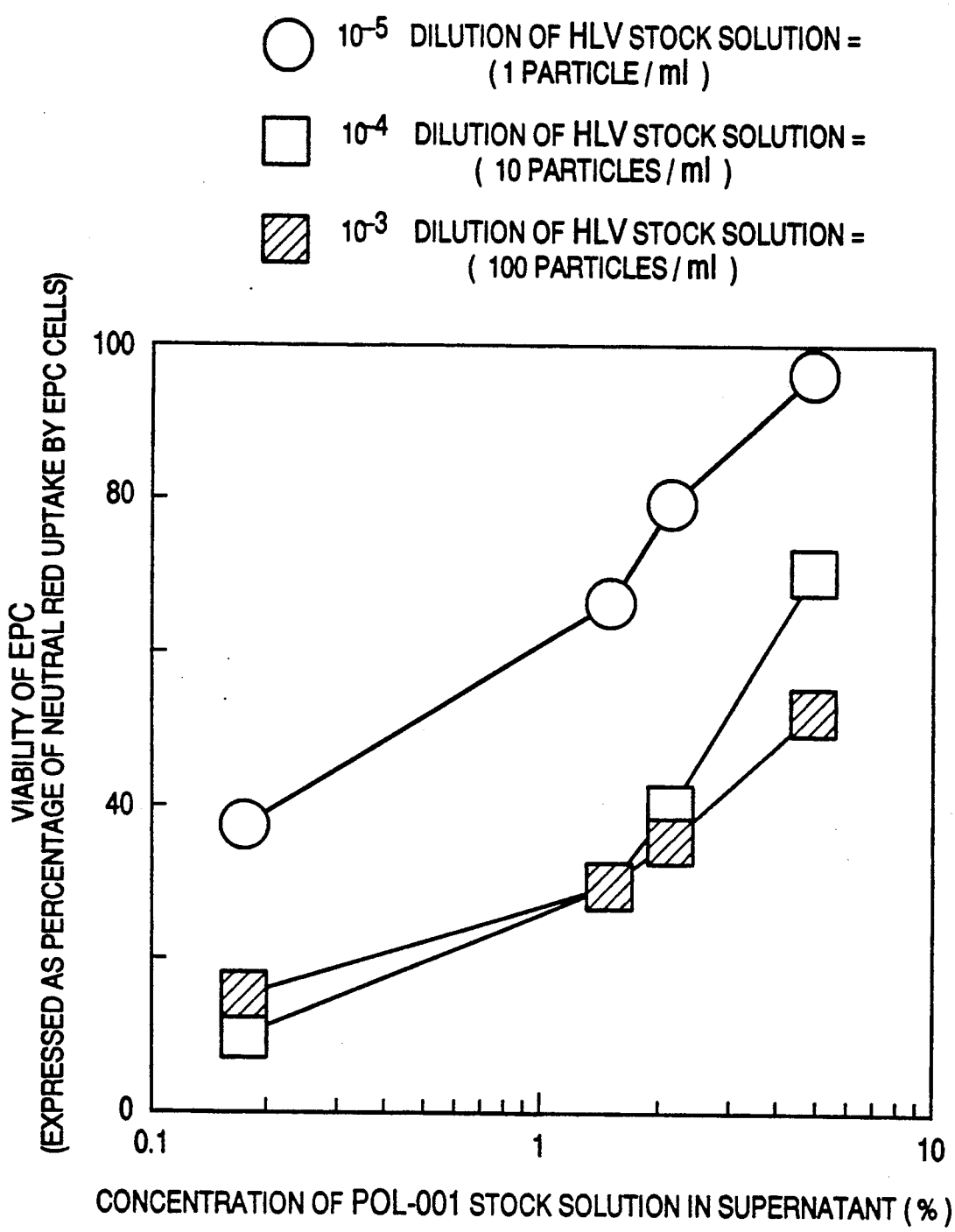
FIG. 2 is a graph illustrating inhibition of HRV infection by physiologically active substances produced by the cell lines of the present invention.

POL-001 was cultured in an ERDF medium containing 10% fetal calf serum at 15° C., 5% $CO_2$ for 72 hours. In the meantime, EPC cells (epithelial cells of salmons) were incubated in an EDRF medium containing 10% fetal calf serum in a 10 ml dish at 15° C., 5% $CO_2$ for 3 days. An increased amount of the supernatant of the POL-001 culture was added the EPC cell cultures: the EPC cell culture contained an increased concentration of the POL-001 supernatant. Halibut rhabdovirus (HRV)[T. Kimura et al., 1987, Dis.Aquat. Org., 1: 209], known as a causative agent of hepatopathy and pancreatopathy of a halibut, was then added to the POL001 treated EPC cell culture at an increased multiplicity of infection (m.o.i.). Neutral red was then added to the cell cultures to a final concentration of 0.01% (v/v). The cell cultures were incubated at 15° C., 5% $CO_2$ for 10 hours. After incubation, the cells was washed with PBS and the viability of the EPC cells was tested by a neutral red intake. FIG. 2 shows the results. The abscissa represents an amount of the supernatant of the POL001 cell culture added to the EPC cell culture and the ordinate represents a viability rate of the EPC cell. The viability rate of the cell was determined by the uptake of neutral red. HRV stock solution contains $1 \times 10^5$ viral particles/ml and $10^{-3}$ or $10^{-5}$ represent a magnitude of the dilution of HRV.

As is shown in FIG. 2, an increased amount of the POL001 cell culture supernatant has increased the viability of the EPC cells, suggesting that the POL001 cells produce immunologically active substances.

What is claimed is:

1. A method of establishing a cell line capable of indefinite growth comprising the steps of isolating a leukocyte from peripheral blood of fish, transforming the leukocyte with at least one expression plasmid containing h-c-myc and c-Ha-ras oncogenes and continuously culturing the cell containing the plasmid.

2. A method of establishing a cell line capable of indefinite growth comprising the steps of isolating a leukocyte from peripheral blood of fish, transforming the leukocyte with at least one expression plasmid containing h-c-fos and c-Ha-ras oncogenes and continuously culturing the cell containing the plasmid.

3. A cell line which is derived from fish leukocytes and is capable of indefinite growth, in which the cell line has been transformed with at least one expression plasmid containing h-c-myc and c-Ha-ras oncogenes.

4. A cell line which is derived from fish leukocytes and is capable of indefinite growth, in which the cell line has been transformed with at least one expression plasmid containing c-fos and c-Ha-ras oncogenes.

* * * * *